United States Patent
Westbye

(10) Patent No.: US 8,791,145 B2
(45) Date of Patent: Jul. 29, 2014

(54) AGRICULTURAL FORMULATIONS WITH ACYL MORPHOLINES AND POLAR APROTIC CO-SOLVENTS

(75) Inventor: Peter Westbye, Stenungsund (SE)

(73) Assignee: Akzo Nobel Chemicals International B.V., Amersfoort (NL)

( * ) Notice: Subject to any disclaimer, the term of this patent is extended or adjusted under 35 U.S.C. 154(b) by 0 days.

(21) Appl. No.: 13/697,170

(22) PCT Filed: May 24, 2011

(86) PCT No.: PCT/EP2011/058460
§ 371 (c)(1),
(2), (4) Date: Jan. 14, 2013

(87) PCT Pub. No.: WO2011/147822
PCT Pub. Date: Dec. 1, 2011

(65) Prior Publication Data
US 2013/0130908 A1    May 23, 2013

Related U.S. Application Data

(60) Provisional application No. 61/348,935, filed on May 27, 2010, provisional application No. 61/348,905, filed on May 27, 2010.

(30) Foreign Application Priority Data

May 27, 2010 (EP) ..................... 10164079
May 27, 2010 (EP) ..................... 10164080

(51) Int. Cl.
| | | |
|---|---|---|
| *A01N 25/02* | (2006.01) | |
| *A01N 37/40* | (2006.01) | |
| *A01N 39/02* | (2006.01) | |
| *A01N 39/04* | (2006.01) | |
| *A01N 43/653* | (2006.01) | |
| *A01P 3/00* | (2006.01) | |
| *A01P 7/00* | (2006.01) | |
| *A01P 13/00* | (2006.01) | |
| *A01P 21/00* | (2006.01) | |

(52) U.S. Cl.
USPC ........... 514/341; 514/383; 514/384; 514/772; 514/788; 514/937; 504/323; 504/324; 504/362; 504/363

(58) Field of Classification Search
USPC ......... 514/772, 936, 341, 383, 384, 788, 937; 504/323, 324, 362, 363
See application file for complete search history.

(56) References Cited

U.S. PATENT DOCUMENTS

| 4,452,630 A | 6/1984 | Dal Moro et al. | |
|---|---|---|---|
| 2002/0068244 A1* | 6/2002 | Machac et al. ............ | 430/331 |

FOREIGN PATENT DOCUMENTS

| DE | 43 41 986 A1 | 6/1995 |
|---|---|---|
| EP | 1 961 301 A1 | 8/2008 |
| GB | 1 299 044 | 12/1972 |
| JP | 7-33605 | 2/1995 |
| JP | 2006-117624 | 5/2006 |
| WO | WO 97/11910 | 4/1997 |
| WO | WO 2006/029736 A1 | 3/2006 |
| WO | WO 2007/028518 A2 | 3/2007 |
| WO | WO 2007/140332 A2 | 12/2007 |
| WO | WO 2008/101620 A2 | 8/2008 |
| WO | WO 2009/025987 A1 | 2/2009 |
| WO | WO 2009/027624 A2 | 3/2009 |
| WO | WO 2009/092795 A1 | 7/2009 |

OTHER PUBLICATIONS

European Search Report for corresponding EP Application No. 10164079.53; Completion date Sep. 28, 2010.
International Search Report and Written Opinion for corresponding PCT Application No. PCT/EP2011/058460; Completion date Feb. 3, 2012.
Database WPI, Week 199515, Thomson Scientific, London, GB; AN 1995-110499, XP-002601846, & JP 7 033605 A (Nihon Noyaku Co Ltd) Feb. 3, 1995 ( English Abstract).
Merlet, S. et al, "Green Solvents for Agrochemicals", Adjuvant Newsletter, vol. 7, Issue 2, Feb. 2010, pp. 1-3.
English Abstract, HCAPLUS, for Chinese Publication No. CN 101380029, Published Oct. 23, 2008.
English Abstract, HCAPLUS, for Japanese Publication No. JP 2006-117624, Published Dec. 27, 2004.
English Abstract, HCAPLUS, for German Publication No. DE 4341986, Published Dec. 9, 1993.

* cited by examiner

*Primary Examiner* — John Pak
(74) *Attorney, Agent, or Firm* — Sugiarto Hadikusumo

(57) ABSTRACT

The present invention provides a formulation comprising a pesticide and/or a plant growth regulator; an acyl morpholine of the formula (I) where R is H, $CH_3$ or $C_2H_5$; and a polar aprotic co-solvent different from an acyl morpholine of formula (I). The formulation can be used in treatment of plants, and is especially well suited for use as a soluble liquid formulation.

(I)

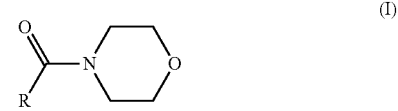

15 Claims, No Drawings

AGRICULTURAL FORMULATIONS WITH ACYL MORPHOLINES AND POLAR APROTIC CO-SOLVENTS

CROSS-REFERENCES TO RELATED APPLICATIONS

This application is a National Stage entry of International Application PCT/EP2011/058460, filed May 24, 2011, which claims the benefit of European Patent Application No. 10164079.5, filed May 27, 2010; U.S. Patent Application No. 61/348,905, filed May 27, 2010; European Patent Application No. 10164080.3, filed May 27, 2010; and U.S. Patent Application No. 61/348,935, filed May 27, 2010. The contents of the aforementioned applications are incorporated herein by reference in their entireties.

TECHNICAL FIELD OF INVENTION

The present invention relates to formulations comprising a pesticide and/or plant growth regulator and a solvent system, methods for the manufacture of such formulations, methods for the treatment of plants using such formulations, and the use of a solvent system as a solvent for a pesticide and/or plant growth regulator.

TECHNICAL BACKGROUND OF THE INVENTION

Agricultural actives, such as pesticides and plant growth regulators, have conventionally been provided to the end-user in different concentrated forms to be diluted in water or other suitable medium to a dilute ready-to-use formulation by the end-user. Such concentrated forms include solid formulations, e.g. powders, and liquid formulations. In many applications, liquid formulations are preferred as problems of dusting of toxic powders and slow dissolution in the diluent may be avoided.

The liquid concentrated formulations include so-called emulsion concentrates and soluble liquid concentrates. An emulsion concentrate comprises an agricultural active, a water-insoluble solvent, and an emulsifier, and when added to the water, it spontaneously, or after mixing, forms an oil-in-water emulsion, the agricultural active primarily being present in the emulsion droplets. This type of concentrated formulation is especially suitable for agricultural actives that are water insoluble/have low water solubility, and where the recommended concentration in the ready-to-use formulation exceeds the solubility of the agricultural active.

A soluble liquid concentrate comprises a water-soluble solvent and agricultural active, and when added to the water, spontaneously, or after mixing, both the solvent and the agricultural active dissolve in the water. This type of concentrated formulation is especially suitable for agricultural actives that are soluble in water also at concentrations exceeding the recommended concentration in the ready-to-use formulation.

When mixing a soluble liquid concentrate with an aqueous medium, initially, there will be a high local concentration of the active before the resulting formulation is equilibrated. Hence, there is a risk for precipitation of the agricultural active occurring when diluting the soluble liquid concentrate in an aqueous medium. This precipitation may pose problems due to slow dissolution of the precipitates. In some cases even, the precipitates are essentially water-insoluble.

WO2007/028518 discloses a soluble liquid formulation of imidacloprid, a neonicotinide insecticide, where N-methyl pyrrolidone (NMP) is used as solvent.

However, NMP has been shown to be a reproductive toxicant (Merlet, S. et al, "Green Solvents for Agrochemicals", Adjuvant Newsletter, vol 7, Issue 2, February 2010, pages 1-3).

One approach to address the problems connected to the use of NMP in Agricultural formulations is described in WO2008/101620, where dialkylamides containing a hydroxysubstituted acyl radical is proposed as a solvent for biocides.

As reported by Merlet, S. et al (supra) however, the solubility of certain commercially interesting biocides, like Imidacloprid, does not have a very high solubility in such dialkylamides containing hydroxysubstituted acyl radicals.

Hence, there is a need in the art to find solvents that can replace NMP in soluble liquid formulations for agricultural actives, while maintaining high solubility of the agricultural actives.

SUMMARY OF THE INVENTION

One object of this invention is to at least partially overcome the drawbacks of the prior art and to provide a solvent system that can be used in soluble liquid formulations and that at least partly can replace the use of NMP.

Another object of the invention is to provide a solvent system for agricultural actives that allows for a concentrated formulation of solvent and agricultural active to be mixed with an aqueous medium without or with only minor precipitation of the active.

The present inventor has surprisingly found that certain short chained acyl morpholines, e.g. N-formyl, N-acetyl and N-propionyl morpholines, can be utilized to meet this object.

Especially, it was found that that a solvent system comprising such short chain acyl morpholine and a polar aprotic co-solvent can be utilized to meet this object.

Hence, in a first aspect, the present invention relates to a formulation comprising a pesticide and/or a plant growth regulator, an acyl morpholine of the formula (I)

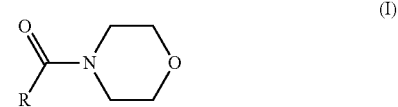

wherein R is H, CH$_3$ or C$_2$H$_5$, and preferably a polar aprotic co-solvent different from an acyl morpholine of the formula (I).

In a second aspect, the present invention relates to a method for producing a formulation as described above containing at least 90% water, by mixing a formulation as described above containing at most 10% water with an aqueous medium.

In a third aspect, the present invention relates to a method for treatment of a plant, comprising contacting said plant with a formulation as described above.

In a fourth aspect, the present invention relates to the use of a formulation of the present invention for treatment of plants.

In a fifth aspect, the present invention relates to the use of an acyl morpholine of the formula (I), or a solvent system comprising an acyl morpholine of the formula (I)

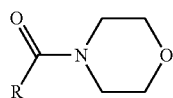

wherein R is H, CH₃ or C₂H₅, and a polar aprotic co-solvent different from an acyl morpholine of formula (I), as a solvent for a pesticide and/or a plant growth regulator.

It is to be noticed that the present invention relates to all possible combinations of the appended claims.

DETAILED DESCRIPTION OF THE INVENTION

A formulation of the present invention comprises.
a) one or more pesticide and/or one or more plant growth regulator;
b) one or more acyl morpholine of formula (I)

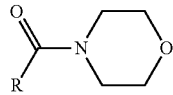

wherein R is H, CH₃ or C₂H₅; and preferably
c) one or more polar aprotic co-solvent different from an acyl morpholine of formula (I).

As used herein, the term "pesticide" refers to an organic compound that will prevent, destroy, repel, or mitigate any pest.

As used herein, the term "plant growth regulator" refers to an organic compound, which through physiological action will accelerate or retard the rate of growth or rate of maturation or otherwise alter the behaviour of ornamental or crop plants or the products thereof.

Pesticides contemplated for use in the present invention include, but are not limited to, fungicides, herbicides, insecticides, miticides, nematicides, acaricides, and molluscicides.

Preferred agricultural actives contemplated for use in the present invention include, but are not limited to, pesticides and plant growth regulators of the classes triazoles, strobilurins, alkylenebis (dithiocarbamate) compounds, benzimidazoles, phenoxy carboxylic acids, benzoic acids, amino acids, sulfonylureas, triazines, triazolineone, pyridine carboxylic acids, neonicotinides, amidines, organophosphates, and pyrethroids.

Examples of fungicides contemplated for use in the present invention include, but are not limited to, fungicides of the classes triazoles (e.g. tebuconazole, tetraconazole, cyproconazole, epoxiconazole, difenconazole, propiconazole, prothioconazole, metconazole), strobilurins (e.g. trifloxystrobin, azoxystrobin, fluoxastrobin, pyraclostrobin), alkylenebis (dithiocarbamate) compounds (e.g. mancozeb) and benzimidazoles (e.g carbendazim).

Examples of herbicides contemplated for use in the present invention include, but are not limited to, phenoxy carboxylic acids (e.g. 2,4-D-acid, MCPA), benzoic acids (e.g. Dicamba-acid), amino acids (e.g glufosinate), sulfonylureas (e.g. methylsulfuron-methyl, rimsulfuron), triazines (e.g. atrazine and simazine), triazolinone (e.g amicarbazone) and pyridine carboxylic acids (e.g. triclopyr).

Examples of insecticides contemplated for use in the present invention include, but are not limited to, neonicotinides (e.g. thiamethoxam, clothianidin, thiacloprid, dinotefuran, acetamiprid, nitenpyram, imidacloprid), amidines (e.g. amitraz), organophosphate (e.g. chlorpyrifos) and pyrethroids (e.g. permethrin, bifenthrin, deltamethrin).

Examples of plant growth regulators contemplated for use in the present invention include, but are not limited to, phosphonic acids (e.g. ethephon), gibberellins cytokinins (e.g. 6-benzylaminopurine) and auxins (e.g. 1-naphtylacetic acid).

A formulation of the present invention preferably comprises a neonicotinide, a phenoxy carboxylic acid, a benzoic acid or a triazole, more preferably imidacloprid.

For a detailed description of each of the above mentioned pesticides and plant growth regulators, reference is made to handbooks, e.g. "The e-Pesticide Manual v4.0" from BCPC Publications Ltd, Alton, Hampshire. (ISBN 1 901396 42 8).

Pesticides and plant growth regulators especially contemplated for use in a formulation of the present invention include those being water soluble at the concentration recommended in a ready-to-use formulation, i.e. the pesticide or plant growth regulator is preferably in solution in the ready-to-use formulation.

In the context of the present invention, water solubility shall be interpreted as being measured according to ASTM E 1148-87 "Standard Test Method for Measurements of Aqueous Solubility".

A formulation of the present invention may comprise a single pesticide or plant growth regulator or may comprise a mixture of two or more different pesticides or two or more plant growth regulators or a mixture of at least one pesticide with at least one plant regulator.

The acyl morpholines contemplated for use in a formulation of the present invention are 4-formyl morpholine (R=H, also referred to as N-formyl morpholine or NFM), 4-acetyl morpholine (R=CH₃, also referred to as N-acetyl morpholine or NAM), 4-propionyl morpholine (R=C₂H₅, also referred to as N-propionyl morpholine or NPM) as well as any mixture of two or more thereof. Preferably, where polar aprotic co-solvents different from the acyl morpholines of general formula (I), are included in the formulation, a formulation of the present invention comprises 4-formyl morpholine, and more preferably, 4-formyl morpholine represents at least 50 wt %, most preferably 100 wt % of the acyl morpholines of formula (I) present in the formulation.

However, for formulations not containing any polar aprotic co-solvents different from the acyl morpholines of general formula (I), and especially for such formulations where the pesticide is N,N'-bis-[(1-formamido-2,2,2-trichloro)ethyl] piperazine, it is preferred that the acyl morpholine is selected from among 4-acetyl morpholine and 4-propionyl morpholine.

The acyl morpholines as such are well known compounds and are commercially available from standard chemical suppliers.

In addition to the acyl morpholine of formula (I), a formulation of the present invention preferably further comprises one or more polar aprotic solvents being different from an acyl morpholine of formula (I), herein referred to as "polar aprotic co-solvent"

The polar aprotic co-solvent is preferably selected from those having a flash point of at least 65° C., as measured according to DIN 51758 "Flash and Fire Points by Cleveland Open Cup Tester".

The polar aprotic co-solvent is preferably selected from the group consisting of a sulfoxide, an amide, a hydrocarbyl- or hydrocarbylene carbonate, and mixtures of two or more thereof. Preferred sulfoxides include dimethyl sulfoxide. Preferred hydrocarbyl carbonates include di-alkyl carbonates, such as those with $C_1$-$C_8$ alkyl chains. Preferred hydrocarbylene-carbonates include alkylene carbonates, more preferably $C_2$-$C_4$-alkylenecarbonates, most preferably propylene carbonate. More preferably, the polar aprotic co-solvent is selected from the group consisting of dimethyl sulfoxide, propylene carbonate and a mixture thereof, most preferably propylene carbonate.

A formulation of the present invention not comprising a polar co-aprotic solvent different from an acyl morpholine of general formula (I) preferably comprises from about 10, more preferably from about 20, most preferably from about 25, to about 70, more preferably to about 60, most preferably to about 50 wt % of a) a pesticide and/or plant growth regulator, and from about 10, more preferably from about 20, most preferably from about 25, to about 90, more preferably to about 80, most preferably to about 70 wt % of b) acyl morpholine of general formula (I).

A formulation of the present invention further comprising a polar aprotic co-solvent different from an acyl morpholine of general formula (I), preferably comprises from about 10, more preferably from about 20, most preferably from about 25, to about 70, more preferably to about 60 and most preferably to about 50 wt % of a) pesticide and/or plant growth regulator; from about 10, more preferably from about 20, most preferably from about 25, to about 89, more preferably to about 80, most preferably to about 70 wt % of b) acyl morpholine of general formula (I) and from about 1, more preferably from about 5, most preferably from about 10 to about 50, more preferably to about 40, most preferably to about 30 wt % of c) polar aprotic solvent different from an acyl morpholine of formula (I), calculated on the basis of the total weight of a), b) and c) in the composition, i.e. not taking water or additional components into account in the calculation.

When a polar aprotic co-solvent different from an acyl morpholine of formula (I) is present, the weight ratio between b) acyl morpholine of formula (I) and c) polar aprotic solvent different from an acyl morpholine of formula (I) is from 5:95, preferably from 30:70, more preferably from 50:50, even more preferably from 70:30, even more preferably from 75:25 and most preferably from 78:22, to 95:5, preferably to 90:10, more preferably to 85:15 and most preferably to 82:18, for example about 80:20.

Especially, when the acyl morpholine of formula (I) is 4-formyl morpholine (N-formyl-morpholine) and the polar aprotic solvent is propylene carbonate, the weight ratio between b) and c) is from 70:30, more preferably from 75:25 and most preferably from 78:22, to 90:10, more preferably to 85:15 and most preferably to 82:18, such as about 80:20.

In currently preferred embodiments, a) is a neonicotinide, preferably imidacloprid, b) is 4-formyl morpholine, and c) is propylene carbonate.

Preferably, a), b) and, when present, c) constitutes from about 60, more preferably from about 70, most preferably from about 80 to 100 wt % of the total weight of the non-water components of the formulation of the invention.

The formulations according to the invention are typically prepared in such a manner that the components are mixed with one another in the desired ratios and to the desired concentrations. In general, the formulations are prepared at a temperature of between 10 and 50° C. Suitable apparatuses that are employed for the preparation of agrochemical formulations are suitable as apparatuses for the preparation of the formulations of the present invention.

In one embodiment, the formulation of the present invention comprises less than 10, preferably less than 5, even more preferably less than 2, and most preferably less than 1 wt % water, based on the total weight of the formulation, such formulation herein after being referred to as a "concentrated formulation".

In such a concentrated formulation of the invention, the concentration of the pesticide or plant growth regulator preferably is at or below the solubility of the pesticide or plant growth regulator in the solvent, i.e. in the combination of acyl morpholine of formula (I) and polar aprotic co-solvent. Hence, the concentrated formulation is preferably a clear homogenous formulation.

In another embodiment, the formulation of the present invention comprises at least 90, preferably at least 95, more preferably at least 99 wt % water, based on the total weight of the formulation, herein after referred to as a "diluted formulation".

In such a diluted formulation, the concentration of the pesticide or plant growth regulator, preferably is at or below the solubility of the pesticide or plant growth regulator in the diluted formulation. Hence, the diluted formulation is preferably a clear homogenous formulation.

A diluted formulation of the present invention typically has a concentration of the pesticide or plant growth regulator matching the concentration recommended for end use, e.g. plant treatment, of the pesticide or plant growth regulator.

A diluted formulation of the invention may be obtained by mixing a concentrated formulation of the invention with an aqueous medium. The aqueous medium is typically tap water.

The concentrated formulation may be added to the aqueous medium, or the aqueous medium may be added to the concentrated formulation. Typically, the former approach is used.

The acyl morpholine of formula (I) and the polar aprotic co-solvent different from an acyl morpholine of formula (I) together forms a solvent system in which the pesticide and/or plant growth regulator is highly soluble.

The acyl morpholines contemplated for use in the present invention have a melting point above room temperature, and are therefore not immediately obvious to use in solvent systems for agricultural formulations that preferably should be in a liquid state at and slightly below normal room temperatures. However, when mixed with the pesticides and/or plant growth regulators, a room temperature liquid composition is typically formed.

The pesticides and plant growth regulators exhibit a high solubility in the acyl morpholines of formula (I). However, when adding a concentrated formulation of pesticide/plant growth regulator and the acyl morpholine, but not containing any polar aprotic co-solvent to an aqueous medium, in some cases, the pesticide/plant growth regulator precipitates. With the addition of the polar aprotic co-solvent to the concentrated formulation, the tendency for precipitation is reduced, and if some precipitate form, it easily dissolves in the resulting, diluted formulation.

4-formyl morpholine and propylene carbonate and/or dimethyl sulfoxide are currently preferred solvent systems for use in the present invention.

In preferred embodiments, a formulation of the present invention is essentially free from, or comprises less than about 5, preferably less than about 2 wt % protic amide solvents.

Those skilled in the art will realise that apart from the pesticide and/or plant growth regulator, the acyl morpholine of formula (I) and the polar aprotic co-solvent, a formulation of the present invention may optionally comprise d) additional components. Examples of such additional components include for example one or more adjuvants, such as bioefficacy enhancers that increase the bioefficacy of agricultural actives, humectants, wetting agents, rheology modifiers, surfactants, stickers, drift reducers and/or other additional components conventionally used in agrochemical compositions.

A formulation of the present invention preferably comprises from 0, more preferably from about 5, most preferably from about 10, to about 40, more preferably to about 30, most preferably to about 20 wt % of additional components d), calculated on the basis of the total weight of a), b), c) and d) in the composition, i.e. not taking any water into account in the calculation.

In preferred embodiments, the formulation of the present invention comprises at least one surfactant. Adding a surfactant to the formulation may prevents the concentrated composition of the invention from staying on the surface of the aqueous medium when added thereto, and may additionally act as adjuvants and/or wetting agents.

Examples of surfactants to be used in the present invention include non-ionic, anionic, amphoteric, zwitterionic, cationic surfactants and mixtures of two or more thereof.

The non-ionic surfactants include, but are not limited to alkoxylated, preferably ethoxylated and/or propoxylated alcohols, preferably containing from 8 to 22 carbon atoms; alkyl(poly)glycosides, such as straight or branched $C_4$-$C_{10}$ alkyl(poly)glycosides; and alkoxylated, preferably ethoxylated, sorbitan or sorbitol esters. Preferred ethoxylated alcohols have a degree of ethoxylation of from 1 to 50, more preferably 2 to 20, most preferably 3 to 10. Some alkoxylated alcohols contemplated for use in the present invention include those based on branched alcohols, such as the Guerbet alcohols, e.g. 2-propylheptanol and 2-ethylhexanol, and $C_{10}$- or $C_{13}$—OXO-alcohols, i.e. an alcohol mixture whose main component is formed by at least one branched $C_{10}$- or $C_{13}$-alcohol, and the alcohols commercially available as Exxal alcohols from Exxon Mobile Chemicals and Neodol alcohols from Shell Chemicals.

The anionic surfactants include, but are not limited to, sulfosuccinates, alkylbenzene sulfonic acid salts, such as calcium or sodium dodecylbenzene sulfonate, alkyl sulphonates, alkyl ether sulphates, phosphate esters of optionally alkoxylated, preferably ethoxylated and/or propoxylated, alcohols, xylene sulfonates and cumene sulfonate salts, naphthalene or alkylnaphthalene sulfonates, which may be condensated.

The cationic surfactants include, but are not limited to alkoxylated, preferably ethoxylated and/or propoxylated fatty amines or ether amines, and alkoxylated, preferably ethoxylated and/or propoxylated quaternary ammonium compounds, such as those commercially available as Berol 556 and Berol R648 (available from Akzo Nobel Surface Chemistry AB, Sweden)

The zwitterionic/amphoteric surfactants include, but are not limited to betaine surfactants, such as alkyl-, alkylamidoalkylene and sulfo betaines, amine oxide surfactants, such as alkyl- and alkylamidoalkylene amine oxides, fatty imino dipropionates and fatty iminoglycinates.

Surfactants may constitute from 0, preferably from about 0.5, more preferably from about 1 to about 20, preferably to about 15, more preferably to about 10 wt % calculated on the basis of the total weight of a), b), c) (when present) and d) in the composition, i.e. not taking water into account in the calculation.

A method for treating a plant represents a separate aspect of the present invention. Such a method comprises the step of contacting said plant with a formulation of the present invention. The formulations of the invention can be applied to the plant by means of spraying, pouring, atomizing, injecting, or brushing on. Preferably, the contacting of the plant is made by means of spraying a diluted formulation as described above.

The application rate of the formulations of the present invention can be varied within a substantial range. The application rate may depend on the pesticide and/or plant growth regulator in the formulation and on their content in the formulation. It is of course desired that the amount of formulation contacted with the plant contain an amount of the pesticide and/or plant growth regulator that is effective to meet the purpose of the formulation.

The formulations of the invention can be used to treat all plants and plant parts. In the context of the present invention, plants are understood as meaning all plants and plant populations, such as desired and undesired wild plants or crop plants, as well as any plant part.

Plant parts are understood as meaning all aerial and subterranean parts and organs of the plant, including shoots, leaves, needles, stalks, stems, flowers, fruiting bodies, fruits, seeds, roots, tubers, and rhizomes. Plant parts also include harvested material and vegetative and generative propagation material, for example cuttings, tubers, rhizomes, slips and seeds.

EXPERIMENTS

Example 1

Solubility in Acyl Morpholines

Various agriculturally active ingredients were dissolved in N-formyl morpholine, N-acetyl morpholine and N-propionyl morpholine in order to evaluate the solubility of the active ingredients in the solvents. This was done by adding the active ingredient to a beaker and thereafter adding the solvent until a clear solution was obtained. The solutions were continually stirred at a temperature of 23° C. during the experiments. When everything had been dissolved, the beakers were left without stirring for 24 h to see if the solution was stable (i.e. no crystallization).

TABLE 1

Dissolution of active ingredients into N-formyl morpholine (NFM), N-acetyl morpholine (NAM), and N-propionyl morpholine (NPM) measured as grams of active ingredient in 100 g solvent.

| Active ingredient | NFM | NAM | NPM | Lactic acid dimethyl amide* |
|---|---|---|---|---|
| Imidacloprid | 30 | 26 | 19 | 14 |
| Amicarbazone | 26 | 24 | 24 | — |
| Dicamba | >100 | >100 | >100 | — |
| MCPA | >100 | >100 | >100 | — |
| Metconazole | >25 | >25 | >25 | — |

*Literature value from Adjuvant Newsletter (supra).

Example 2

Dilution of Imidacloprid Formulation in Water

Formulations containing 200 g/l of Imidacloprid was formulated together with 40 g/l of an alcohol ethoxylate (2-propylheptanol ethoxylated with 8 moles of EO per mole of alcohol) and diluted to a final volume of one liter with each one of the solvents N-formyl morpholine, N-acetyl morpholine and N-propionyl morpholine along with a co-solvent. The co-solvents used were dimethylsulfoxide (DMSO), propylene carbonate (PC), dimethylformamide (DMF) and ethyl lactate (EL). Ethyl lactate is a protic solvent and is included in the experiment for comparison. The amount of each co-solvent, in % by weight of the total weight of morpholine and co-solvent, is seen in table 2. The solutions was diluted in water to an end concentration of imidacloprid of 0.4 g/l and the dilution was judged by ocular inspection with the naked eye, and in the table below, the following is used:
+: easily dissolved,
−: permanent crystals.
NS: Non soluble

TABLE 2

Crystallization of Imidacloprid upon dilution in water from concentrated solutions (200 g/l) of imidacloprid dissolved in N-formyl morpholine (NFM), N-acetyl morpholine (NAM), and N-propionyl morpholine (NPM) together with a cosolvent (i.e. dimethylsulfoxide (DMSO), propylene carbonate (PC), dimethyl formamide (DMF) or ethyl lactate (EL).

| Solvent | Cosolvent | 0% Cosolvent | 5% | 10% | 15% | 20% | 25% | 30% | 50% | 95% |
|---|---|---|---|---|---|---|---|---|---|---|
| NFM | DMSO | − | − | + | + | + | + | + | + | + |
|  | PC | − | − | − | + | + | + | NS | NS | NS |
|  | DMF | − | − | − | + | + | + | + | + | + |
|  | EL | − | − | NS | NS | NS | NS | NS | NS | NS |
| NAM | DMSO | − | − | − | + | + | + | + | + | + |
|  | PC | − | − | − | − | NS | NS | NS | NS | NS |
|  | DMF | − | − | − | − | + | + | + | + | + |
|  | EL | − | − | NS | NS | NS | NS | NS | NS | NS |
| NPM | DMSO | − | NS | NS | NS | NS | − | − | + | + |
|  | PC | − | NS | NS | NS | NS | NS | NS | NS | NS |
|  | DMF | − | NS | NS | NS | NS | NS | − | + | + |
|  | EL | − | NS | NS | NS | NS | NS | NS | NS | NS |

Example 3

Dilution of Amicarbazone Formulation in Water

In an experiment similar to Example 2 above, formulations containing 100 g/L of Amicarbazone was formulated together with 40 g/L of an alcohol ethoxylate (2-propylheptanol ethoxylated with 8 moles of EO per mole of alcohol) and diluted to a final volume of one liter with each of the solvents N-formyl morpholine and N-acetyl morpholine along with a co-solvent. The co-solvents used were propylene carbonate (PC), dimethylformamide (DMF) and ethyl lactate (EL). The amount of each co solvent, in % by weight of the total weight of morpholine and co-solvent, can be seen in table 2. The solutions were diluted in local tap water to an end concentration of 7 g/L and the dilution was judged by ocular inspection with the naked eye, and in the table below the following is used:
+ No crystals
− Permanent crystals

TABLE 3

Crystallization of Amicarbazone upon dilution in water from concentrated solutions (100 g/L) of Amicarbazone dissolved in N-formyl morpholine (NFM) and N-acetyl morpholine (NAM) together with a co-solvent, i.e. propylene carbonate (PC), dimethyl formamide (DMF) or ethyl lactate (EL) respectively.

| Solvent | Cosolvent | 0% Cosolvent | 5% | 10% | 20% | 30% | 50% | 95% |
|---|---|---|---|---|---|---|---|---|
| NFM | PC | − | − | − | + | − | − | − |
|  | DMF | − | − | − | − | − | − | + |
|  | EL | − | − | − | − | − | − | − |
| NAM | PC | − | − | − | − | − | − | − |
|  | DMF | − | − | − | − | − | − | + |
|  | EL | − | − | − | − | − | − | − |

Example 4

Differential Scanning Calorimetry (DSC)

To monitor the enthalpy of evaporation differential scanning calorimetry was used. The reason for these measurements was to determine the cohesion forces between N-formyl morpholine and propylene carbonate. The mixtures (N-formyl morpholine/propylene carbonate in different ratio) were scanned from 20° C. to 300° C. with a temperature increase of 5° C./minute, using a DSC1 calorimeter from Mettler Toledo with STARe software. The results from the DSC measurements can be seen in table 4. From the results it evident that a blend of 80/20 N-formyl morpholine/propylene carbonate (w/w) show a significant decrease in enthalpy of evaporation, i.e. the mixture has a minimum in enthalpy of evaporation at or close to this ratio.

TABLE 4

Enthalpy of evaporation at various weight ratios between N-formyl morpholine (NFM) and propylene carbonate (PC).

| Weight ratio NFM:PC | Enthalpy of evaporation (J/g) |
|---|---|
| 100:0 | 382 |
| 95:5 | 421 |
| 90:10 | 433 |
| 85:15 | 405 |
| 80:20 | 331 |
| 75:25 | 369 |
| 50:50 | 366 |
| 0:100 | 392 |

The invention claimed is:
1. A formulation comprising:
a) a pesticide and/or a plant growth regulator;
b) 4-formyl morpholine; and
c) propylene carbonate.
2. A formulation according to claim 1, wherein the weight ratio between 4-formyl morpholine and propylene carbonate is from 70:30 to 90:10.
3. A formulation according to claim 1, wherein said pesticide or plant growth regulator is selected from the group consisting of triazoles, strobilurins, alkylenebis (dithiocarbamate) compounds, benzimidazoles, phenoxy carboxylic acids, benzoic acids, amino acids, sulfonylureas, triazines, triazolinones, pyridine carboxylic acids, neonicotinides, amidines, organophosphates, pyrethroids, phosphonic acids, gibberellins, cytokinins, auxins and mixtures of two or more thereof.

4. A formulation according to claim 1, wherein said pesticide and/or plant growth regulator is a neonicotinide.

5. A formulation according to claim 4, wherein said neonicotinide is imidacloprid.

6. A formulation according to claim 1, comprising:
from 10 to 70 wt % of a);
from 10 to 89 wt % of b); and
from 1 to 50 wt % of c), based on the total weight of a), b) and c) in the formulation.

7. A formulation according to claim 1, further comprising d) at least one additional component selected from the group consisting of adjuvants, surfactants, wetting agents, rheology modifiers and mixtures of two or more thereof.

8. A formulation according to claim 7, comprising from 5 to 40 wt % of d) based on the total weight of a), b), c) and d) in the formulation.

9. A formulation according to claim 1, comprising at most 10 wt % water.

10. A formulation according to claim 1, comprising at least 90 wt % water.

11. A method of treating a plant, comprising contacting said plant with a formulation according to claim 1.

12. A method of solubilising a pesticide and/or plant growth regulator, the method comprising mixing 4-formyl morpholine and propylene carbonate with the pesticide and/or plant growth regulator.

13. The method according to claim 12 wherein the weight ratio between 4-formyl morpholine and propylene carbonate is from 70:30 to 90:10.

14. The method according to claim 12, wherein said pesticide and/or plant growth regulator is neonicotinide.

15. The method according to claim 14, wherein said neonicotinide is imidacloprid.

\* \* \* \* \*